United States Patent
Batz-Sohn et al.

(10) Patent No.: US 6,191,297 B1
(45) Date of Patent: Feb. 20, 2001

(54) PROCESS FOR THE PREPARATION OF ORGANOSILANES FUNCTIONALIZED IN THE 3-POSITION

(75) Inventors: Christoph Batz-Sohn, Hanau; Ralf Karch, Kleinostheim; Steffen Seebald, Grosskrotzenburg; Matthias Prinz, Freigericht, all of (DE)

(73) Assignee: Degussa-Huls AG, Frankfurt, am Main (DE)

( * ) Notice: Under 35 U.S.C. 154(b), the term of this patent shall be extended for 0 days.

(21) Appl. No.: 09/329,371

(22) Filed: Jun. 10, 1999

(30) Foreign Application Priority Data

Jun. 10, 1999 (DE) ............................................... 198 25 793

(51) Int. Cl.⁷ ....................................................... C07F 7/04
(52) U.S. Cl. .......................................... 556/479; 556/478
(58) Field of Search ..................... 556/414, 415, 556/427, 445, 446, 449, 478, 479, 482, 484, 485, 487

(56) References Cited

U.S. PATENT DOCUMENTS

| 3,439,014 | * | 4/1969 | Patton et al. | 556/450 |
| 4,503,160 | * | 3/1985 | Williams, Jr. | 502/158 |
| 4,533,744 | * | 8/1985 | Williams, Jr. | 556/479 |

OTHER PUBLICATIONS

CA:94:175250 abs of JP5514693, Nov. 1980.*

* cited by examiner

*Primary Examiner*—Jean F. Vollano
(74) *Attorney, Agent, or Firm*—Pillsbury Winthrop LLP

(57) ABSTRACT

A process for the preparation of organosilanes functionalized in the 3-position, by the reaction of suitable allyl compounds with hydrogen silanes, using platinum catalysts having one or more sulfur-containing ligands.

9 Claims, No Drawings

PROCESS FOR THE PREPARATION OF ORGANOSILANES FUNCTIONALIZED IN THE 3-POSITION

CROSS-REFERENCE TO RELATED APPLICATION

This application is related to German Application DE 198 25 793.7, filed Jun. 10, 1998, which disclosure is incorporated herein by reference.

FIELD OF THE INVENTION

The present invention provides a process for the platinum-catalyzed preparation of 3-functionalized propylsilanes from hydrogen silanes and allyl compounds.

BACKGROUND OF THE INVENTION

It is known that hydrogen silanes can be reacted, for example, with allyl chloride in the presence of homogeneous or heterogeneous platinum catalysts to form 3-chloropropylsilanes. This reaction is generally referred to as hydrosilylation (see, for example, equation I).

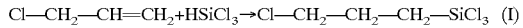

The process is termed homogeneous hydrosilylation when soluble platinum compounds, in the simplest case, for example, $H_2PtCl_6 \cdot 6H_2O$, are used as catalysts (cf. DE-OS 28 51 456, CS-PS 176 910, U.S. Pat. No. 4,292,433, U.S. Pat. No. 4,292,434, DE-AS 11 87 240, DE-PS 11 65 028); heterogeneous hydrosilylations utilize elemental platinum or platinum compounds on a support (cf. U.S. Pat. No. 2,637,738, DE-PS 20 12 229, DE-PS 28 15 316).

It is also known that in the reaction of, for example, allyl chloride with hydrogen silanes to form 3-chloropropylsilanes, a portion of the allyl chloride used reacts with the hydrogen silane in a side reaction with the formation of propylene and of the chlorosilane corresponding to the respective hydrogen silane (see, for example, equation II).

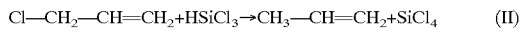

Thus, for example, in the reaction of allyl chloride with trichlorosilane, 25–30 mol. % of the allyl chloride entering into the reaction is converted by this side reaction into propylene, accompanied by the formation of equivalent quantities of silicon tetrachloride. The molar ratio of chloropropylsilane formed to silicon tetrachloride in the crude product is a measure of the selectivity of the reaction and typically attains values of between 2.33:1 (70% yield, based on allyl chloride) and 3:1 (75% yield). It is also known that the formation of propylene can be lessened by a special reaction procedure in pressurized apparatus. However, the result of this procedure is that the propylene obtained in the side reaction undergoes a further quantitative reaction with the hydrogen silane used, with the formation of propylsilanes. Even in the reactions carried out in the conventional manner under normal pressure, the propylene originating from the side reaction largely enters into a further side reaction with hydrogen silane to form the corresponding propylsilanes (cf. also DE 34 04 703 C) (see, for example, equation 3).

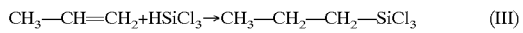

Thus, for example, in an industrial plant, in a heterogeneously catalyzed reaction of allyl chloride and trichlorosilane in a column packed with platinized activated carbon, up to 230 kg propyltrichlorosilane is obtained per 1000 kg 3-chloropropyltrichlorosilane, which indicates an additional requirement for approximately 28% of trichlorosilane, based on the quantity of trichlorosilane which has entered the target product (cf. also DE 41 19 994 A1).

Apart from the additional requirement for hydrogen silane, the problem with such processes is also the complicated separation of the unwanted propylsilanes, for which there are scarcely any other fields of use and which consequently have to be disposed of by expensive methods.

SUMMARY OF THE INVENTION

According to this invention, the 3-functionalized propylsilanes are obtained by addition of allyl compounds corresponding to the general formula I

wherein X can be Cl, Br, I, F, CN, SCN, SH, SR, OH, $NRR^1$ or OR, wherein R and $R^1$, each independently of one another, denote $(C_1-C_6)$alkyl or $(C_3-C_7)$aryl, to silanes corresponding to formula II

wherein $R^2$, $R^3$, $R^4$, each independently of one another, denote hydrogen, halogen, $(C_1-C_6)$alkyl, $(C_1-C_6)$haloalkyl, $(C_3-C_6)$allyl, $(C_1-C_4)$alkoxy, phenyl, aryl or aralkyl, at reaction temperatures of between 0° C. and 200° C. and at pressures of between 800 mbar and 6 bar and in the presence of a platinum catalyst having one or more sulfur-containing ligands.

It is preferable that X denotes a halogen, in particular chlorine.

The procedure is practicable at normal pressure, at excess pressure and under a partial vacuum. It is preferable to operate at pressures of between 800 mbar and 6 bar. A pressure of from 800 mbar to 2 bar is particularly suitable.

The procedure according to the invention is usefully carried out in such a way that the allyl compound and the hydrogen silane used in slight excess are reacted in a suitable vessel together with the catalyst at temperatures of between 0° C. and 200° C., until all the allyl chloride has reacted.

The silanes which according to the invention can be used as starting component include silanes corresponding to the structural type II

wherein $R^2$, $R^3$ and $R^4$, each independently of one another, are hydrogen, halogen, $(C_1-C_6)$alkyl, $(C_1-C_6)$alkoxy, $(C_1{-}14$ $C_6)$haloalkyl, $(C_3-C_6)$allyl, phenyl, aryl or aralkyl. Silanes used in the reaction according to the invention are preferably silanes such as trichlorosilane, or mixed substituted silanes such as, for example, methyl, ethyl, propyl hydrogen dichlorosilane or dimethyl hydrogen chlorosilane.

The platinum catalyst employed can be used in any oxidation state. In principle, the catalyst can be prepared beforehand and added to the reaction mixture, or can be produced in the actual reaction mixture (in situ). The catalysis can take place either homogeneously or heterogeneously, that is, the platinum compound used can also be attached to a support (cf. U.S. Pat. No. 2,637,738, DE-PS 20 12 229, DE-PS 28 15 316). The catalyst can be present either in stoichiometric or in catalytic quantities, for example, from 0.1 to 10000 ppm, preferably between 10 and 500 ppm, based on the allyl compound used. The preparation of platinum compounds in general is described in "Gmelins Handbuch der Anorganischen Chemie, eighth edition, volume 68, Part D ("Komplexverbindungen [des Platins] mit neutralen Liganden").

In order to achieve the action according to the invention, the catalyst must have a sulfur-containing ligand. In this connection it is sufficient for the sulfur-containing ligand to form a simple donor/acceptor interaction with the platinum nucleus. The sulfur-containing ligand can be monodentate or polydentate and can be a sulfide, sulfoxide, sulfane, polysulfane or thiol or in general be a sulfur compound in which the sulfur is present in the formal oxidation state of -II. The person skilled in the art knows of such compounds from the literature (Houben-Weyl, volume E11, G. Thieme Verlag, Stuttgart 1985, in particular, pages 158ff, 669ff, 129ff, 147ff, 32ff). The sulfur-containing compounds can be used individually or in any mixture. The process according to the invention therefore covers sulfur-containing ligands of the following structural type:
$R^5SR^6$, $R^7S(O)R^8$, $R^9S_ZR^{10}$, $R^9S_ZR^{10}S_Y$—$R^{11}$ wherein $R^5$, $R^6$, $R^7$, $R^8$, $R^9$, $R^{10}$, $R^{11}$ can be any organic group or H, and Z, Y can each be integers between 2 and 6. Examples of the ligands which can be used are sulfanes,
such as ethyl methyl sulfide,
ethyl phenyl sulfide, allyl phenyl sulfide,
benzyl-2,2,2-trifluoroethyl sulfide,
bis(2-mercaptoethyl) sulfide,
bis(trimethylsilylmethyl) sulfide,
2-chloroethyl methyl sulfide, 2-chloroethyl phenyl sulfide,
2-chloro-3,4-dimethyl-5-phenyl-1,3,2-oxazaphospholidine 2-sulfide, chlorodimethyl sulfide, chloromethyl phenyl sulfide,
diethyl sulfide, diallyl sulfide, dibenzyl sulfide, dibutyl sulfide, di-tert.-butyl sulfide, dimethyl sulfide, dioctyl sulfide, diphenyl sulfide, dipropyl sulfide,
2-hydroxyethyl methyl sulfide, 2-hydroxyethyl phenyl sulfide, phenyl vinyl sulfide, phosphorus sesquisulfide, propylene sulfide, tetraethylthiuram disulfide, tetramethylthiuram disulfide, tris(methylthio)methane,
bis[3-(triethoxysilyl)propyl] sulfide, cyclic sulfanes such as 1,4-oxathiane, 2,5-dihydroxy-1,4-dithiane, 1,3-dithiane, 1,3-dithiane-2-carboxylic ethyl ester, hexamethyldisilathiane,
2-methyl-1,3-dithiane, thianthrene,
2-trimethylsilyl-1,3-dithiane, 1,3,5-trithiane, tetrahydrothiophene, trimethylene sulfide,
1,4,7-trithiacyclononane, 1,4,7,-trithiacyclodecane, di- and polysulfanes, such as
bis(2-nitrophenyl) disulfide,
bis[3-(triethoxysilyl)propyl]tetrasulfide,
bis[3-(triethoxysilyl)propyl] disulfide, diallyl disulfide, dibenzyl disulfide, di-tert.-butyl disulfide, dibutyl disulfide, dimethyl disulfide, diphenyl disulfide, dipropyl disulfide, sulfoxides, such as allyl phenyl sulfoxide, chloromethyl phenyl sulfoxide, dibenzyl sulfoxide, dimethyl sulfoxide, diphenyl sulfoxide,
ethyl ethylthiomethyl sulfoxide, DL-methionine sulfoxide, methyl methylthiomethyl sulfoxide,
methylphenyl sulfoxide, R(+)-methyl-p-tolyl sulfoxide, S(-)-methyl-p-tolyl sulfoxide, phenyl vinyl sulfoxide, tetrahydrothiophene-1-oxide, thiophenes such as thiophene, 2-acetylthiophene, 3-acetylthiophene, 2-ethylthiophene, DL-alpha-aminothiophene-2-acetic acid, 1-benzothiophene, 2,5-bis(5-tert.-butylbenzoxazol-2-yl)thiophene,
2,2'-bithiophene, 2-bromothiophene, 3-bromothiophene, 2-chlorothiophene, 2,3-dibromothiophene,
3,4-dibromothiophene, 6,7-dihydro-4-benzo[b]thiophenone,
2,5-dimethylthiophene,
2-hydroxymethylthiophene, 2-iodothiophene,
3-methoxythiophene, 2-methylthiophene, 3-methylthiophene,
3-methylthiophene-2-carbaldehyde,
5-methylthiophene-2-carbaldehyde,
5-methylthiophene-2-carboxylic acid, 2,2',5',2"-terthiophene,
thiophene-2-acetonitrile, thiophene-3-acetonitrile,
thiophene-2-acetylchloride, thiophene-2-carbaldehyde,
thiophene-3-carbaldehyde, thiophene-2-carboxylic acid,
thiophene-3-carboxylic acid, thiophene-2-carbonyl chloride,
thiophene-2-acetic acid, thiophene-3-acetic acid,
thiophene-2-acetic acid methyl ester, 2-thiophenethiol,
thiazoles such as thiazole, 2-acetylthiazole, 2-aminobenzothiazole,
2-amino-5-nitrothiazole,
2-(4-aminophenyl)-6-methylbenzothiazole, 2-aminothiazole,
2-amino-2-thiazoline,
2-amino-4-thiazolylacetic acid ethyl ester,
2,2'-azinobis(3-ethylbenzothiazoline-6-sulfonic acid),
benzothiazole,
3-(benzothiazol-2-ylthio)-1-propanesulfonic acid,
2-bromothiazole, 2-chlorobenzothiazole,
2,3-dihydro-3,3-dimethyl-1,2-benzisothiazol-1,1-dioxide,
2,5-dimethylbenzothiazole,
2,2'-dithiobis(4-methylthiazole),
2-fluoro-3,3-dim.-2,3-dihyd.-1,2-benzisothiazole-1,1-dioxide,
5-(2-hydroxyethyl)-4-methylthiazole,
3-hydroxy-4-methyl-2(3H)-thiazolethione,
2-mercaptobenzothiazole, 2-mercapto-2-thiazoline,
2-methylbenzothiazole, 2-(methylmercapto)-2-thiazoline,
2-methylnaphtho(1,2-d)thiazole, 5-methylthiazole,
2-methyl-2-thiazoline, R(-)-2-oxothiazolidine-4-carboxylic acid,
succinyl sulfathiazole, L-thiazolidine-4-carboxylic acid,
2,4-thiazolidinedione, 1-(2-thiazolylazo)-2-naphthol,
4-(2-thiazolylazo)resorcinol,
R(-)-2-thioxothiazolidine-4-carboxylic acid,
2-(trimethylsilyl)thiazole.
Preferred sulfur-containing ligands are in particular diethyl sulfide, dimethyl sulfoxide, tetrahydrothiophene, benzothiazole, thiophene, dibenzyl disulfide, 1,3-dithiane, tris(methylthio)methane, dimethyl sulfide, dibenzyl sulfide, diallyl sulfide. The term "alkyl" means both "straight-chain" and "branched" alkyl groups. The term "straight-chain alkyl group" means, for example, groups such as methyl, ethyl, n-propyl, n-butyl, n-pentyl, n-hexyl and the term "branched alkyl group" means groups such as, for example, isopropyl or tert.-butyl. The term "halogen" denotes fluorine, chlorine, bromine or iodine. The term "alkoxy" denotes groups such as, for example, methoxy, ethoxy, propoxy, butoxy, isopropoxy, isobutoxy or pentoxy.

Within the context of the invention, "aryl" means phenyls, biphenyls or other benzenoid compounds substituted with $(C_1–C_6)$alkyl, $(C_1–C_6)$alkoxy, halogen or hetero atoms such as N, O, and phenols, P or S. By "arylalkyl" it is meant that the "aryl" described above is bonded to the corresponding silicon atom by a $(C_1–C_6)$alkyl chain, which in turn can be $(C_1–C_4)$alkyl- or halogen-substituted. If the "aryl" contains a hetero atom such as O or S, then the $(C_1 14 C_6)$alkyl chain can also form a bond with the silicon atom via the hetero atom.

Where substituents such as, for example, $(C_1–C_4)$alkoxy, are specified, the number in the subscript denotes the total number of carbon atoms in the group.

DETAILED DESCRIPTION OF THE PREFERRED EMBODIMENTS

The following Examples 1 to 4 illustrate the process according to the invention. Examples 5 to 7 are Comparative Examples.

Here the selectivity given means the molar ratio of the required product 3-chloropropyltrichlorosilane (Cl-PTS) to silicon tetrachloride. The ratio of the selectivities achieved and the yield of 3-chloropropyltrichlorosilane obtained in the Examples according to the invention demonstrate the superiority of the new process over conventional processes (cf. Comparative Examples 5 to 7).

EXAMPLES

Example 1

100 g (472 mmol) 3-chloropropyltrichlorosilane, 76.6 g (1 mol) allyl chloride and 142.3 g (1.05 mol) trichlorosilane were mixed together in a 500 ml three-necked flask equipped with mushroom-shaped heater, magnetic stirrer, internal thermometer and reflux condenser which had been intensively cooled to −30° C. 37.0 mg (0.10 mmol) DMSO $(C_2H_4)PtCl_2$ (V. Y. Kukushkin et al, Inorg. Chim. Acta 185 (1991), 143) was added thereto and the mixture was heated to boiling point. In the course of the reaction the internal temperature rose, owing to the conversion of the low-boiling components to higher-boiling products. The reaction was terminated when the boiling temperature remained constant at a high level for a relatively long time. The reaction mixture was then cooled and the mixture of products formed was analyzed by gas chromatography. After the removal of the 3-chloropropyltrichlorosilane used as solvent, the product was found to have the following composition:

| | |
|---|---|
| 2.12 wt. % | trichlorosilane (TCS) |
| 0.04 wt. % | allyl chloride (ACl) |
| 16.72 wt. % | silicon tetrachloride (STC) |
| 2.73 wt. % | propyltrichlorosilane (PTS) |
| 78.38 wt. % | 3-chloropropyltrichiorosilane (Cl-PTS) |

Therefore the value found for the selectivity of the reaction, based on the quantity of materials, is 3.76:1, which corresponds to a yield of 79.0% 3-chloropropyltrichlorosilane, based on allyl chloride.

Examples 2 to 4

Various other homogeneous catalysts were used under conditions similar to those described in Example 1. The results obtained are shown in the Table below.

| Catalyst, Quantity | Composition of product (wt. %) | Selectivity (Yield relative to allyl chloride) |
|---|---|---|
| Ex. 2 | 44.0 mg (0.10 mmol) THT$_2$PtCl$_2$ (THT = Tetrahydro-thiophene, E. G. Cox et al., J. Chem. Soc. A (1934), 182) | TCS: 0.04 ACl: 0.13 STC: 17.80 PTS: 1.50 Cl-PTS: 80.36 | 3.62: 1 (78.4%) |
| Ex. 3 | 42.0 mg (0.10 mmol) DMSO$_2$PtCl$_2$ (Dimethyl sulfoxide, J. H. Pierce et al, Inorg. Chem. 11 (1972), 1280) | TCS: 2.14 ACl: 0.05 STC: 18.23 PTS: 213 Cl-PTS: 77.36 | 3.40: 1 (77.3%) |
| Ex.4 | 45.0 mg (0.10 mmol) (Et$_2$S)$_2$PtCl$_2$ | TCS: 1.03 ACl: 0.02 | 3.40: 1 (77.3%) |

| Catalyst, Quantity | Composition of product (wt. %) | Selectivity (Yield relative to allyl chloride) |
|---|---|---|
| (E. G. Cox et al., J. Chem. Soc. A (1934), 182) | STC: 18.46 PTS: 2.09 Cl-PTS: 78.37 | |

Examples 5 to 7 (Comparative Examples)

Various other homogeneous catalysts were used under conditions similar to those described in Example 1. The results obtained are shown in the Table below.

| Catalyst | Composition product | Selectivity (yield relative to allyl chloride) |
|---|---|---|
| Ex. 5 | H$_2$PtCl$_6$ × 6 H$_2$O (CPA), 41 mg | TCS: 0.15 ACl: 1.67 STC: 21.71 PTS: 3.54 Cl-PTS: 72.88 | 2.69: 1 (72.9%) |
| Ex. 6 | (Ph$_3$P)$_2$PtCl$_2$ (P. J. Stang et al., J. Organomet. Chem. 388 (1990), 215) | TCS: 1.78 ACl: — STC: 22.77 PTS: 2.14 Cl-PTS: 73.78 | 2.60: 1 (72.2%) |
| Ex. 7 | CPA (0.1 M in i-Propanol), 0.2ml + dppe(0.1 M in PhH), 0.1 ml | TCS: 1.19 ACl: — STC: 20.12 PTS: 1.45 Cl-PTS: 77.06 | 3.07: 1 (75.4%) |

What is claimed is:

1. A process for the preparation of propyl silanes having a functional group in the 3-position, comprising:
    adding allyl compounds corresponding to formula (I)

$$H_2C=CH—CH_2X \quad \quad (I)$$

wherein X can be Cl, Br, I, F, CN, SCN, SH, SR, OH, NRR$^1$ or OR, wherein R and R$^1$, each independently of one another, denote (C$_1$–C$_6$)alkyl or (C$_3$–C$_7$)aryl,
    to silanes corresponding to formula (II)

$$R^2R^3R^4SiH \quad \quad (II)$$

wherein R$^2$, R$^3$, R$^4$, each independently of one another, denote hydrogen, halogen, (C$_1$–C$_6$)alkyl, (C$_1$–C$_6$) haloalkyl, (C$_3$–C$_6$)allyl, (C$_1$–C$_4$)alkoxy, phenyl, aryl or aralkyl, at reaction temperatures of between 0° C. and 200° C. and at pressures of between 800 mbar and 6 bar and in the presence of a platinum catalyst which has a platinum atom nucleus and one or more sulfur-containing ligands, wherein the one or more ligands are selected from the group consisting of sulfoxides, thiophenes and thiazoles.

2. The process according to claim 1, wherein X is F, Cl, Br, or I.

3. The process according to claim 2, wherein X is Cl.

4. The process according to claim 1, wherein the silane of formula II is selected from the group consisting of trichlorosilane, methyl hydrogen dichlorosilane, ethyl hydrogen dichlorosilane, propyl hydrogen dichlorosilane and dimethyl hydrogen chlorosilane.

5. The process according to claim 1, wherein the sulfur-containing ligand is monodentate or polydentate and is a sulfoxide.

6. The process according to claim 5 wherein the sulfur-containing ligand comprises a member selected from the group consisting of: dimethyl sulfoxide, tetrahydrothiophene, benzothiazole, thiophene, and mixtures thereof.

7. The process according to claim 1, wherein concentration of the catalyst is between 0.1 and 10,000 ppm, based on the allyl compound.

8. The process according to claim 1, comprising:
carrying out the reaction at pressures of between 800 mbar and 2 bar.

9. The process according to claim 1, wherein the concentration of the catalyst is between 10 and 500 ppm, based on the allyl compound.

* * * * *